(12) United States Patent
Brito De La Fuente et al.

(10) Patent No.: US 10,143,674 B2
(45) Date of Patent: Dec. 4, 2018

(54) COMPOSITION COMPRISING EPA AND DHA TRIGLYCERIDES FOR PARENTERAL ADMINISTRATION

(71) Applicant: Fresenius Kabi Deutschland GmbH, Bad Homburg (DE)

(72) Inventors: Edmundo Brito De La Fuente, Friedrichsdorf (DE); Crispulo Gallegos-Montes, Bad Homburg (DE); Lida A. Quinchia-Bustamente, Bad Homburg (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/114,988

(22) PCT Filed: Jan. 28, 2015

(86) PCT No.: PCT/EP2015/051657
§ 371 (c)(1),
(2) Date: Jul. 28, 2016

(87) PCT Pub. No.: WO2015/113987
PCT Pub. Date: Aug. 6, 2015

(65) Prior Publication Data
US 2016/0338987 A1 Nov. 24, 2016

(51) Int. Cl.
| | | |
|---|---|---|
| A61K 31/232 | (2006.01) | |
| A61K 9/00 | (2006.01) | |
| A61K 47/10 | (2017.01) | |
| A61K 47/12 | (2006.01) | |
| A61K 47/24 | (2006.01) | |
| A61K 9/107 | (2006.01) | |
| A23L 33/12 | (2016.01) | |

(52) U.S. Cl.
CPC ........... *A61K 31/232* (2013.01); *A23L 33/12* (2016.08); *A61K 9/0029* (2013.01); *A61K 9/107* (2013.01); *A61K 47/10* (2013.01); *A61K 47/12* (2013.01); *A61K 47/24* (2013.01)

(58) Field of Classification Search
CPC ...... A61K 31/232; A61K 47/10; A61K 47/12; A61K 47/24; A61K 9/107; A61K 9/0029
See application file for complete search history.

(56) References Cited

U.S. PATENT DOCUMENTS 5,874,470 A 2/1999 Nehne
2011/0206741 A1* 8/2011 Lee ...................... A61K 9/0019
424/400
(Continued)

FOREIGN PATENT DOCUMENTS

CN 102 512 367 6/2012
CN 102512367 A * 6/2012 ........... A61K 31/202
(Continued)

OTHER PUBLICATIONS

CN 102512367, Weiping Yu, Formula of novel docosahexaenoic acid (DHA fat emulsion preparation and prepartionmethod thereof, 2012, English translation, 15 pages (Year: 2012).*
(Continued)

*Primary Examiner* — Yate' K Cutliff
(74) *Attorney, Agent, or Firm* — Hylton-Rodic Law PLLC

(57) ABSTRACT

Described herein are compositions that include an aqueous phase and 5 to 30%, by weight, of an oil phase, based on the total weight of the composition. The oil phase comprises the omega-3 fatty acid triglyceride eicosapentaenoic acid triglyceride, docosahexaenoic acid triglyceride, or mixtures thereof. The composition further comprises at least one amphoteric surfactant, at least one co-surfactant, and at least one co-solvent. The compositions comprise less than 0.03% by weight of sodium oleate, based on the total weight of the composition. Also described are methods for preparing such compositions as well as such compositions for use as a medicament, in particular for use in treating stroke, sepsis, Alzheimer's disease or cancer. Also featured are methods of treating these conditions by parenterally administering a composition to a patient in need and methods of providing
(Continued)

parenteral nutrition to such patients by administering to them a composition as described herein.

9 Claims, 1 Drawing Sheet

(56) References Cited

U.S. PATENT DOCUMENTS

2012/0196934 A1* 8/2012 Hustvedt .............. A61K 9/4858
514/560
2012/0277316 A1* 11/2012 Tillman ................ A61K 9/0095
514/547

FOREIGN PATENT DOCUMENTS

| CN | 102 552 328 | | 7/2012 | |
|---|---|---|---|---|
| CN | 102552328 | * | 7/2012 | ........... A61K 31/185 |
| WO | 2010/104575 | | 9/2010 | |

OTHER PUBLICATIONS

CN 102552328, Yuwang Pharmaceutical Co., Ltd, Preparation of compund fish oil nano emulsion, 2012, English translation, English translation, 9, pages (Year 2012).*

Lu, et al. "Physico-chemical properties of marine phospholipid emulsions." *Journal of the American Oil Chemists' Society* 89.11 (2012): 2011-2024.

* cited by examiner

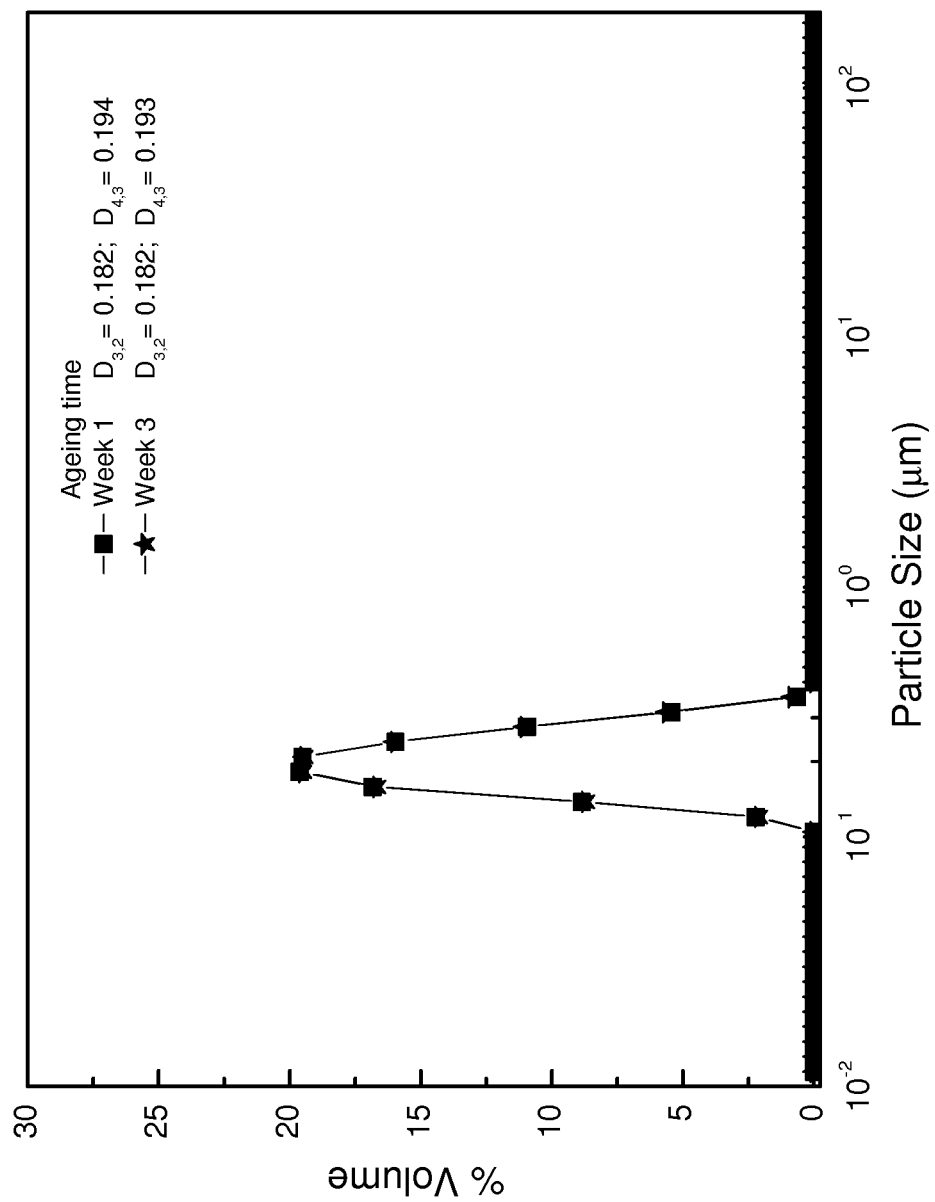

COMPOSITION COMPRISING EPA AND DHA TRIGLYCERIDES FOR PARENTERAL ADMINISTRATION

CROSS REFERENCE TO RELATED APPLICATIONS

This application is a U.S. national stage application of International Application No. PCT/EP2015/051657, filed on Jan. 28, 2015, which claims priority to European Application No. 14152785.3, filed on Jan. 28, 2014. The contents of these previously filed applications are hereby incorporated by reference herein in their entirety.

Description

The present invention relates to a composition for parenteral administration comprising an aqueous phase and 5 to 30% by weight of an oil phase, based on the total weight of the composition, wherein the oil phase comprises omega-3 fatty acid triglycerides selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, and wherein the composition comprises less than 0.03% by weight of sodium oleate, based on the total weight of the composition. Further, the present invention relates to a method for preparing such a composition as well as to such a composition for use as a medicament, in particular for use in treating stroke, sepsis, Alzheimer's disease or cancer. Furthermore, the present invention relates to a method for treating stroke, sepsis, Alzheimer's disease or cancer comprising parenterally administering such a composition to a patient in need thereof and to a method of providing parenteral nutrition to a patient suffering from at least one disease selected from stroke, sepsis, Alzheimer's disease or cancer, the method comprising administering such a composition to the patient.

Oil-in-water parenteral emulsions have been used clinically for nutritional and medical purposes for several years. Of the various types of oils used, historically soybean oil and safflower oil were first introduced almost 50 years ago and thus, with these oils the greatest clinical experience exists. These lipids provide a rich source of non-glucose based calories, essential fatty acids, such as omega-6 fatty acids, vitamins E and K and the like. However, their high proportions of omega-6 fatty acids have raised concerns about their administration as the sole lipid source to critically ill patients and patients with compromised immune function such as patients suffering from sepsis or trauma.

High levels of omega-6 fatty acids have been considered to increase production of mediators which have been correlated with immunosuppressive actions such as impaired reticular endothelial system function and inhibition of lymphocytes, macrophages, and neutrophil functions. Furthermore, the high number of double bonds in omega-6 fatty acids makes them prone to lipid peroxidation.

Meanwhile, fish oils, which are rich in long chain omega-3 fatty acids, and their use in enteral and parenteral nutrition have received attention in the scientific literature and industrial area because of their reported positive role in human health. The potential benefits of omega-3 fatty acids in a diet include reduced risk of several diseases including cardiovascular diseases, hypertension, atherosclerosis, inflammatory and autoimmune disorders. The polyunsaturated fatty acids in fish oils, especially eicosapentaenoic acid (EPA) and docosahexaenoic acid (DHA), have been shown to have a positive effect on preventing a variety of human diseases and disorders. In fish oil, DHA and EPA can be present in a mono-, di-, or triglyceridic form.

Some emulsions which comprise fish oils are thus already known in the art:

For example, WO 87/02247 A1 describes a lipid emulsion of fish oils comprising high concentrations of omega-3 fatty acid esters and low concentrations of free fatty acids for intravenous administration for the treatment of thrombotic disease states.

Further, presently, there are a few commercially available parenteral lipid emulsions containing omega-3 fatty acids derived from fish in clinical use in Europe. The first product available on the market was Omegaven™ (Fresenius Kabi), a 10% fish oil-in-water emulsion. The second product, Lipoplus™ (B. Braun), is a physical mixture of oils of medium chain triglycerides or MCT (50%), soybean (40%) and fish oil (10%). The most recent product is SMOFlipid™ (Fresenius Kabi), and is also a physical mixture of oils: soybean oil (30%), MCT oil (30%), olive oil (25%) and fish oil (15%).

However, unrefined fish oils also contain saturated fatty acids as well as other impurities such as sterols, waxes, lipid soluble vitamins, phenols and other constituents. Accordingly, fish oils must be purified prior to consumption. In addition, fish oils are known to degrade during processing and in storage.

Further, in order to obtain the benefits from omega-3 fatty acids present in these fish oils, a high amount of most emulsions described in the art may need to be consumed due to their comparatively low amount of omega-3 fatty acids. This overconsumption however may increase the intake of cholesterol and saturated fatty acids which may possibly have deleterious health effects.

Thus, emulsions comprising a higher concentration of omega-3 fatty acids when compared to emulsions which comprise fish oil were proposed in the art. Such emulsions with a high amount of omega-3 fatty acids, however, often tend to be unstable.

For example, WO 2011/103512 A1 describes the preparation of an emulsion comprising an emulsifier, a tonicity agent and a docosahexaenoic acid free fatty acid (DHA-FFA) wherein the emulsion is substantially free of eicosapentaenoic acid (EPA) and derivatives thereof. The emulsion is described to be suitable for parenteral administration.

WO 2010/104575 A2 describes emulsions comprising an oil phase comprising a fish oil enriched in omega-3 fatty acid triglycerides, such as eicosapentaenoic acid triglyceride and docosahexaenoic acid triglyceride, together with medium chain triglycerides, wherein the amount of the medium chain triglycerides within the oil component of the emulsion is in the range of from 10 to 40% by weight. These emulsions comprise, besides phospholipids, sodium oleate as emulsifier.

WO 2011/103514 A1 relates to emulsions for parenteral administration comprising an emulsifier, a tonicity agent and about 100 mg/ml to about 300 mg/ml docosahexaenoic acid triglyceride, wherein the emulsion is substantially free of eicosapentaenoic acid and eicosapentaenoic acid derivatives.

WO 2011/133841 A2 describes 20% oil-in-water emulsions, wherein the oil phase comprises at least one omega-3 essential fatty acid selected from a group consisting of alpha-linolenic acid (ALA), eicosapentaenoic acid (EPA), and docosahexaenoic acid (DHA). Further, the oil phase comprises medium chain triglycerides (MCT). Such MCTs are considered to be convenient in order to enhance the stability of such emulsions (see Driscoll D F, Nehne J, Peterss H et al. The influence of medium-chain triglycerides on the stability of all-in-one formulations. *Int J Pharm.* 2002; 240:1-10).

However, due to the presence of MCTs in most of these emulsions, the amount of omega-3 fatty acids in these emulsions is still not very high. Thus, in order to obtain the benefits from omega-3 fatty acids, also a comparatively high amount of these emulsions needs to be administered.

Thus, there is still the need for stable emulsions with a high concentration of omega-3 fatty acids and optimum bioavailability for parenteral administration.

SUMMARY OF THE INVENTION

The present invention relates to a composition for parenteral administration comprising an aqueous phase and 5 to 30% by weight of an oil phase, based on the total weight of the composition, wherein the oil phase comprises omega-3-fatty acid triglycerides selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, and wherein the composition comprises less than 0.03% by weight of sodium oleate, based on the total weight of the composition.

Furthermore the present invention relates to a method for preparing a composition for parenteral administration and to a composition obtained or obtainable by said method, the composition comprising an aqueous phase and 5 to 30% by weight of an oil phase, based on the total weight of the composition, wherein the oil phase comprises omega-3 fatty acids selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, wherein the method comprises:
(a) providing an aqueous phase comprising the at least one co-solvent and the at least one amphoteric surfactant,
(b) providing an oil phase comprising omega-3 fatty acid triglycerides selected from the group consisting of eicosapentaenoic acid triglyceride, docosahexaenoic acid triglyceride and mixtures thereof,
(c) mixing the oil phase according to (b) with the aqueous phase according to (a),
wherein the at least one co-surfactant is added either in step (b) or in step (c), and wherein less than 0.03% by weight of sodium oleate based on the total weight of the final composition are added during the method.

In a further aspect, the present invention relates to a composition as described above, or to a composition obtainable or obtained by the above described method, for use as a medicament, in particular for use in treating stroke, sepsis, Alzheimer's disease or cancer. In a further aspect, the present invention relates to a composition as described above, or to a composition obtainable or obtained by the above described method, for use in providing parenteral nutrition to a patient suffering from at least one disease selected from stroke, sepsis, Alzheimer's disease or cancer.

DETAILED DESCRIPTION

It was found that an emulsion comprising the combination of omega-3 fatty acid triglycerides and at least one amphoteric surfactant, at least one co-surfactant and at least one co-solvent and comprising less than 0.03% by weight of sodium oleate based on the total weight of the final composition, is surprisingly stable even with a comparatively high amount of omega-3 fatty acid triglycerides within the composition. It is contemplated that with this composition an advantageous decrease in the necessary dosage as compared to, for instance, fish oil or other compositions known in the art is possible, in particular due to the possibility of providing such stable emulsions being highly enriched in eicosapentaenoic acid triglycerides and/or docosahexaenoic acid triglycerides.

Oil in Water Emulsion

As described above, the composition according to the present invention and the composition obtained or obtainable by the above described method comprises an aqueous phase and 5 to 30% by weight of an oil phase. Preferably, the composition comprises 5 to 25% by weight of an oil phase, more preferably 5 to 20% by weight of an oil phase, more preferably 5 to 15% by weight of an oil phase, more preferably 5 to 10% by weight of an oil phase, more preferably around 9 to 10% by weight of an oil phase.

As to the aqueous phase, this phase preferably comprises water in a purity suitable for intravenous administration.

The amount of water is preferably in the range of from 95 to 70% by weight, preferably 95 to 75% by weight, more preferably 95 to 80% by weight, more preferably 90 to 80% by weight.

Preferably, the composition according to the invention is an emulsion, in particular an oil-in-water emulsion.

In case the emulsion is an oil-in-water emulsion, the oil droplets preferably have a mean particle size ($D_{4,3}$) in the range of from 0.1 µm to 0.3 µm, preferably of from 0.15 µm to 0.25 µm, measured with an LS 13 320 Laser Diffraction Particle Size Analyser (Beckman Coulter) according to USP <729>.

DHA and EPA

As defined above, the oil phase comprises omega-3 fatty acid triglycerides selected from the group consisting of eicosapentaenoic acid triglycerides, docosahexaenoic acid triglycerides and mixtures thereof.

The term "eicosapentaenoic acid (EPA) triglycerides" as used herein refers to triglycerides of (5Z,8Z,11Z,14Z,17Z)-5,8,11,14,17-icosapentaenoic acid, also known as 20:5(n-3). EPA is a an omega-3 fatty acid with a 20-carbon chain and five cis double bonds; the first double bond is located at the third carbon from the omega end.

The term docosahexaenoic acid (DHA) triglycerides as used herein refers to triglycerides of all-cis-docosa-4,7,10,13,16,19-hexa-enoic acid, also known as is 22:6(n-3). DHA is an omega-3 fatty acid that is a primary structural component of the human brain, cerebral cortex, skin, sperm, testicles and retina. Docosahexaenoic acid is a 22-carbon chain with six cis double bonds, the first double bond being located at the third carbon from the omega end.

Preferably, at least 60% by weight of the oil phase, such as of from 60% by weight to 95% by weight of the oil phase, more preferably at least 65% by weight of the oil phase, more preferably at least 70% by weight of the oil phase, more preferably at least 75% by weight of the oil phase, more preferably at least 80% by weight of the oil phase, more preferably of from 85 to 90% by weight of the oil phase, present in the composition according to the invention or in the composition obtained or obtainable by the method as described above consists of eicosapentaenoic acid triglyceride, docosahexaenoic acid triglyceride or a mixture thereof.

In particular, the oil phase comprises a mixture of eicosapentaenoic acid triglycerides and docosahexaenoic acid triglycerides, wherein the weight ratio of eicosapentaenoic acid triglycerides relative to all docosahexaenoic acid triglycerides is preferably in the range of from 1:9 to 9:1.

The EPA and DHA triglycerides may be obtained by any way known to those skilled in the art.

It is known that docosahexaenoic acid (DHA) and eicosapentaenoic acid (EPA) and the derivatives thereof are contained per se, or in the form of glycerides and in the form of other derivatives, in natural fats and oils, particularly in fats and oils of aquatic animals (e.g., fish, marine mammals, and crustaceans such as krill and other euphausiids), animal tissues (e.g., brain, liver, eyes, etc.) and animal products such as eggs or milk.

Thus, for example, they may be extracted from animal sources including aquatic animals (e.g., fish, marine mammals, and crustaceans such as krill and other euphausiids), animal tissues (e.g., brain, liver, eyes, etc.) and/or animal products such as eggs or milk.

Some methods for the isolation of these docosahexaenoic acid (DHA) and eicosapentaenoic acid (EPA) and their derivatives and their conversion to pure docosahexaenoic acid (DHA) triglycerides and eicosapentaenoic acid (EPA) triglycerides are described in the art.

Such isolation by purification can be achieved by any means known to those of skill in the art and can include the extraction, e.g. by supercritical fluid extraction, of an oil from an organism which produces DHA and/or EPA and the subsequent purification via chromatographic methods. Alternatively, the oils can be extracted using extraction techniques such as are described in U.S. Pat. No. 6,750,048. Additional extraction and/or purification techniques are taught e.g. in WO2001076715 and WO/2001/076385.

As to the weight ratio of eicosapentaenoic acid triglycerides relative to docosahexaenoic acid triglycerides, this weight ratio is preferably in the range of from 1:9 to 9:1, such as 1:9, 1:8, 1:7, 1:6, 1:5, 1:4, 1:3, 1:2, 1:1, 2:1, 3:1, 4:1, 5:1, 6:1, 7:1, 8:1 or 9:1.

Medium Chain Fatty Acid Derivatives

Preferably, the oil phase present in the composition, described above, comprises less than 1% by weight, more preferably less than 0.5% by weight, more preferably less than 0.1% by weight, more preferably less than 0.05% by weight, more preferably less than 0.01% by weight, more preferably essentially no, more preferably no, medium chain fatty acid derivatives, wherein this amount refers to the sum of all medium chain fatty acid derivatives present and is based on the total weight of the oil phase. The term "essentially no" in this context refers to an amount <0.01% by weight including 0% by weight.

The term "medium chain fatty acid derivative" as used hereinunder and above refers to fatty acid derivatives, such as mono-, di- or triglycerides (MCT), comprising a medium chain fatty acid or alkyl esters of medium chain fatty acids these fatty acids being 6 to 12 carbon atoms in length. Medium chain fatty acids include but are not limited to caproic acid, caprylic acid, capric acid and lauric acid.

Surprisingly, it has been found that stable compositions may be provided without these medium chain fatty acid derivatives which, due to the fact that MCTs may be omitted, may comprise an even higher amount of EPA derivatives and DHA derivatives. This finding is particularly surprising since the prior art emphasizes that omega-3 fatty acid comprising compositions should contain MCTs to enhance their stability.

Thus, the present invention also relates to a composition as described above, or to a composition obtainable or obtained by the above described method, wherein the oil phase comprises less than 1% by weight, more preferably less than 0.5% by weight, more preferably less than 0.1% by weight, more preferably less than 0.05% by weight, more preferably less than 0.01% by weight, more preferably essentially no, more preferably no, medium chain fatty acid derivatives.

Surfactant

As described above, the composition comprises at least one amphoteric surfactant. The term "surfactant" as used within the meaning of the present invention refers to compounds which stabilize the composition by reducing the interfacial tension between the oil phase and the water phase and which typically comprise at least one hydrophobic group (their tail) and at least one hydrophilic group (their head). These surfactants (which may also be referred to as emulsifiers) are preferably used in amounts effective to provide, optionally together with further surfactants present, stable and even distribution of the oil phase within the aqueous phase. In particular, these surfactants are selected from surfactants which have been approved for parenteral administration.

The term "amphoteric surfactant" refers to surfactants which carry a charge that varies depending on the pH of the solution. At low pH (acidic conditions), they act as cationic surfactants while at high pH (basic), they act as anionic surfactants. When both charge groups are permanent, the surfactants are sometimes also called zwitterionic.

Preferably, the at least one amphoteric surfactant is lecithin. Within the meaning of the present invention the term "lecithin" refers to a naturally occurring or synthetic lecithin that may be suitably refined. Suitable lecithins include, but are not limited to, lecithins derived from egg, corn or soybean or mixtures thereof. Further suitable lecithins include, but are not limited to, dihexanoyl-L-alpha-lecithin, dioctanoyl-L-alpha-lecithin, didecanoyl-L-alpha-lecithin, didodecanoyl-L-alpha-lecithin, ditetradecanoyl-L-alpha-lecithin, dihexadecanoyl-L-alpha-lecithin, dioctadecanoyl-L-alpha-lecithin, dioleoyl-L-alpha-lecithin, dilinoleoyl-L-alpha-lecithin and alpha-palmitol. Lecithins are typically mixtures of diglycerides of fatty acids linked to the choline ester of phosphoric acid and can contain differing amounts of other compounds depending on the method of isolation. Typically, commercial lecithin is a mixture of acetone-insoluble phosphatides. Preferably, the lecithin is obtained from egg or from seeds including soybean and corn, using methods well known in the art. Lecithin obtained from soybean is referred to herein as soy lecithin. Lecithin obtained from egg is referred to herein as egg lecithin.

Preferably, the composition comprises lecithin as amphoteric surfactant, more preferably the lecithin is selected from the group consisting of egg lecithin, soy lecithin, and mixtures thereof.

As to the soy lecithin, said soy lecithin typically comprises at least 50% by weight of phospholipids, more preferably of from 50 to 95% by weight, more preferably of from 70 to 80% by weight and most preferably of from 75 to 85% by weight, based on the total weight of the soy lecithin. The soy lecithin, as described above, usually comprises at least phosphatidylcholine and phosphatidylethanolethanolamine, and usually further comprises phosphatidylinositol and phosphatidic acid. A typical composition comprises phosphatidylcholine in an amount in the range of from 70% by weight to 80% by weight and phosphatidylethanolethanolamine in an amount in the range of from 5 to 10% by weight, based on the total weight of the soy lecithin. Such soy lecithin is commercially available, for example as Epikurin™170.

As to the egg lecithin, said egg lecithin typically comprises at least 50% by weight of phospholipids, preferably at least 80% by weight, more preferably at least 90% by weight, based on the total weight of the egg lecithin.

The egg lecithin, as described above, usually also comprises phosphatidylcholine, phosphatidylethanolethanolamine, phosphatidylinositol and phosphatidic acid. A typical composition comprises phosphatidylcholine in an amount in the range of from 60 to 85% by weight and phosphatidylethanolethanolamine in an amount in the range of from 7 to 18% by weight, based on the total weight of the egg lecithin. Such egg lecithins are commercially available, for example as PL 90 or Lipoid E80.

It is to be understood that lecithin may be employed in combination with other amphoteric surfactants. Preferably, the composition only comprises lecithin as amphoteric surfactant.

Thus, the present invention also relates to a composition for parenteral administration comprising an aqueous phase and 5 to 30% by weight of an oil phase based on the total weight of the composition, wherein the oil phase comprises omega-3 fatty acid triglycerides selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, wherein the at least amphoteric surfactant is lecithin, and wherein the co-solvent is polyethylene glycol and/or propylene glycol, and wherein the composition comprises less than 0.03% by weight of sodium oleate based on the total weight of the composition. Further, the present invention relates to a method for preparing a composition as described above as well as to a composition obtained or obtainable by the above described method, the composition comprising an aqueous phase and 5 to 30% by weight of an oil phase based on the total weight of the composition, wherein the oil phase comprises omega-3 fatty acids selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, wherein the at least one amphoteric surfactant is lecithin, and wherein the co-solvent is polyethylene glycol and/or propylene glycol, wherein the method comprises:
(a) providing an aqueous phase comprising the at least one co-solvent and the at least one amphoteric surfactant,
(b) providing an oil phase comprising omega-3 fatty acid triglycerides selected from the group consisting of eicosapentaenoic acid triglyceride, docosahexaenoic acid triglyceride and mixtures thereof,
(c) mixing the oil phase according to (b) with the aqueous phase according to (a),
wherein the at least one co-surfactant is added either in step (b) or in step (c), and wherein less than 0.03% by weight of sodium oleate based on the total weight of the final composition are added during the method.

The total amount of amphoteric surfactants within the composition, more preferably of lecithin, is preferably in the range of from 0.5 to 5% by weight, more preferably 0.75 to 3% by weight, more preferably in the range of from 1% by weight to 2% by weight, such as 1.0, 1.1, 1.2, 1.3, 1.4, 1.5, 1.6, 1.7, 1.8, 1.9 or 2.0% by weight, based on the total weight of the composition.

Co-Solvent

As described above, the composition comprises at least one co-solvent. The term co-solvent refers to molecules that may increase the stability of the composition according to the invention. In addition to making the environment more hydrophobic by reducing the dielectric constant of water, co-solvents increase the amount of molecularly dispersed surfactant in the aqueous phase. Availability of free surfactant aids in the solubilisation of hydrophobic molecules by creating pockets of hydrophobic regions within the aqueous phase.

Examples of co-solvents include ethanol, propylene glycol and polyethylene glycol (PEG).

Preferably, the at least one co-solvent is a polyalkylene glycol or an alkylene glycol, preferably polyethylene glycol or propylene glycol, more preferably polyethylene glycol.

Thus, the present invention also relates to a composition for parenteral administration comprising an aqueous phase and 5 to 30% by weight of an oil phase based on the total weight of the composition, wherein the oil phase comprises omega-3 fatty acid triglycerides selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, wherein the composition comprises less than 0.03% by weight of sodium oleate, based on the total weight of the composition, and wherein the at least one co-solvent is a polyalkylene glycol or an alkylene glycol, preferably polyethylene glycol or propylene glycol, more preferably polyethylene glycol. Further, the present invention relates to a method for preparing such a composition as well as to such a composition for use as a medicament, in particular for use in treating stroke, sepsis, Alzheimer's disease or cancer.

It is to be understood that polyethylene glycol may be employed in combination with other co-solvents such as any one of the co-solvents mentioned above. Preferably, the composition only comprises polyethylene glycol and/or propylene glycol as co-solvent.

In case polyethylene glycol is employed as co-solvent, the polyethylene glycol preferably has a mean molecular weight in the range of from 100 to 20000 Da, more preferably in the range of from 200 to 1000 Da, more preferably in the range of from 300 to 600 Da, most preferably around 400 Da.

Preferably, the co-solvent is selected from the group consisting of PEG 200, PEG 300, PEG 400, PEG 600, PEG 1000, PEG 1450, PEG 3350, PEG 4000, PEG 6000, PEG 8000 and PEG 20000. Most preferably, the co-solvent is PEG 400.

Preferably, the total amount of co-solvents present ranges from 0.1 to 2.0% by weight, more preferably from 0.25 to 1.75% by weight, more preferably from 0.50 to 1.50% by weight, more preferably from 0.70 to 1.40% by weight, more preferably from 0.80 to 1.30% by weight, and even more preferably from 0.90 to 1.20% by weight, based on the total weight of the composition.

Surprisingly, it has been found that emulsions comprising polyethylene glycol and/or propylene glycol as well as lecithin are particularly stable.

Co-Surfactant

As described above, the composition comprises at least one co-surfactant. A co-surfactant is an amphiphilic molecule, i.e. a molecule that contains both hydrophilic and lipophilic groups. Usually a co-surfactant substantially accumulates with the surfactant at the interfacial layer. The hydrophile-lipophile balance (HLB) number is used as a measure of the ratio of hydrophilic and lipophilic groups present in a surfactant or co-surfactant, respectively. Usually a co-surfactant with a very low HLB value (thus with a relatively high affinity to oil) is used together with a surfactant with a high HLB to modify the overall HLB of the system. Unlike surfactant, the co-surfactant may not be capable of forming self-associated structures, like micelles, on its own. Several kinds of molecules including nonionic surfactants, alcohols, amines and acids, can function as co-surfactants in a given system. The quantity of a co-surfactant in a system is usually less than that of the surfactant and it often serves to modify the overall HLB value of the system. The co-surfactant has the effect of further reducing the interfacial tension, whilst increasing the fluidity of the interface. Co-surfactants may also adjust the curvature of the interfacial film by partitioning between the tails of the surfactant chains, allowing greater penetration of the oil between the surfactant tails.

Preferably, the at least one co-surfactant is an unsaturated fatty acid, preferably an omega-9 fatty acid, more preferably a monounsaturated omega-9 fatty acid, more preferably oleic acid.

The total amount of at least one co-surfactant is preferably in the range of from 0.01 to 1% by weight, more preferably in the range of from 0.02% by weight to 0.5% by weight, more preferably in the range of from 0.03% by weight to 0.25% by weight, based on the total weight of the composition.

Thus, the present invention also relates to a composition for parenteral administration comprising an aqueous phase and 5 to 30% by weight of an oil phase based on the total weight of the composition, wherein the oil phase comprises omega-3 fatty acid triglycerides selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, wherein at least one co-surfactant is oleic acid, and wherein the composition comprises less than 0.03% by weight of sodium oleate based on the total weight of the composition. Further, the present invention relates to a method for preparing such a composition as described above and to a composition obtained or obtainable by said method, wherein the at least one co-surfactant is oleic acid. Further, the present invention relates to a composition for use as a medicament, in particular for use in treating stroke, sepsis, Alzheimer's disease or cancer and for use in providing parenteral nutrition to a patient suffering from at least one disease selected from stroke, sepsis, Alzheimers disease and cancer, as described above, wherein the at least one co-surfactant is oleic acid. Surprisingly, it has been found that emulsions comprising oleic acid in combination with a co-solvent and an amphoteric surfactant are particularly stable.

Preferably, the composition as described above comprises oleic acid as co-surfactant, lecithin as amphoteric surfactant and polyethyleneglycol and/or propylene glycol as co-solvent(s).

Other Surfactants

It is noted that the composition as described above may comprise any other suitable surfactant or any other co-surfactant provided that the composition comprises less than 0.03% by weight of sodium oleate based on the total weight of the composition. As suitable other surfactants, e.g. nonionic or anionic surfactants may be mentioned. Thus, also in the method described above, any other surfactant such as e.g. nonionic or anionic surfactants may be added, such as in particular in step (a), provided that less than 0.03% by weight of sodium oleate based on the total weight of the final composition are added during the method.

Preferably, the composition comprises less than 0.02% by weight, more preferably less than 0.01% by weight, more preferably essentially no sodium oleate, preferably no sodium oleate.

The term "essentially no" is denoted to mean that essentially no, that is an amount of <0.01% by weight including 0% by weight, sodium oleate, preferably 0% by weight, is added to the composition during the preparation process. It is noted that in case oleic acid is added to the mixture during the preparation of the composition, and in case any further sodium salts, such as sodium hydroxide, are added during the preparation process, it may not be ruled out that at least a portion of this oleic acid is being transformed into its corresponding sodium salt, i.e. into sodium oleate, even though it is contemplated that substantially all of the oleic acid should be present in the oil phase and that should thus not be transformed to the corresponding sodium salt. Such minor amount of sodium oleate which may be formed is thus included in term "essentially no".

Thus, the present invention also relates to a composition for parenteral administration comprising an aqueous phase and 5 to 30% by weight of an oil phase, based on the total weight of the composition, wherein the oil phase comprises omega-3 fatty acid triglycerides selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, and wherein the composition comprises less than 0.02% by weight, more preferably less than 0.01% by weight, more preferably essentially no sodium oleate, preferably no sodium oleate. Further, the present invention relates to a method for preparing such a composition as well as to such a composition obtained or obtainable by said method, wherein less than 0.02% by weight, more preferably less than 0.01% by weight, more preferably essentially no sodium oleate, preferably no sodium oleate is added during the method.

Tonicity Agent

Tonicity agents are substances which are used to confer tonicity to e.g. pharmaceutical compositions.

Preferably, the composition according to the invention comprises at least one tonicity agent.

A tonicity agent useful in the present composition can be any pharmaceutically acceptable tonicity agent. Common tonicity agents include, but are not limited to, agents selected from the group consisting of sodium chloride, mannitol, lactose, dextrose (hydrous or anhydrous), sucrose, glycerol, and sorbitol, and solutions of the foregoing.

Thus, according to a preferred embodiment of the invention, the present invention also relates to a composition, as described above, as well as to a composition obtained or obtainable by the above described method, wherein the composition comprises at least one tonicity agent.

Preferably, the tonicity agent is glycerol.

If present, preferably the total amount of tonicity agents present is in the range of 0 to 10% by weight, more preferably from 1 to 5% by weight, more preferably from 1 to 4% by weight, more preferably from 1 to 3% by weight, more preferably from 1.5 to 2.8% by weight, and even more preferably from 2.0. to 2.5% by weight, based on the total weight of the composition.

Preferably, the composition has an osmolality in the range 305 to 420 mOsmol/kg, more preferably in the range of from 300 to 420 mOsmol/kg, measured with a Vapor Pressure Osmometer, Model 5520 (Vapro™) according to USP <785>.

Antioxidant

Preferably, the composition according to the invention comprises at least one agent with antioxidant activity, preferably at least two agents with antioxidant activity.

An antioxidant useful in the present composition can be any pharmaceutically acceptable compound having antioxidant activity including sodium metabisulfite, sodium bisulfite, sodium sulfite, sodium thiosulfate, sodium formaldehyde sulfoxylate, sodium formaldehyde bisulfite, thioglycerol, thiosorbitol, thioglycolic acid, cysteine hydrochloride, n-acetyl-cysteine, citric acid, alpha-tocopherol, beta-tocopherol, gamma-tocopherol, Trolox (soluble form of vitamin E), butylated hydroxyanisole (BHA), butylated hydroxytoluene (BHT), t-butylhydroquinone (TBHQ), monothioglycerol, propyl gallate, lopurinol, carnosine, histidine, enzymes, such as superoxide dismutase, catalase, selenium glutathione peroxidase, phospholipid hydroperoxide and glutathione peroxidase, Coenzyme Q 10, tocotrienols, carotenoids, quinones, bioflavonoids, polyphenols, bilirubin, ascorbic acid, isoascorbic acid, uric acid, metal-binding proteins, ascorbic acid palmitate, an antioxidant obtained or obtainable from rosemary and rosemary extract.

The at least one agent with antioxidant activity is in particular selected from the group consisting of alpha-tocopherol, beta-tocopherol, gamma-tocopherol, ascorbic acid, and mixtures of two or more thereof.

If present, the total amount of agents with antioxidant activity is preferably in the range of from 0.01 to 0.05% by weight, more preferably from 0.01 to 0.04% by weight, more preferably from 0.01 to 0.03% by weight, and even more preferably from 0.015 to 0.025 by weight, based on the total weight of the composition.

Thus, the present invention also relates to a composition as described above as well as to a composition obtained or obtainable by the above described method, wherein the composition comprises at least one agent with antioxidant activity. Preferably, the composition further comprises at least one tonicity agent.

More preferably, the composition comprises at least two different agents with antioxidant activity. For example, the present invention comprises alpha-tocopherol and beta-tocopherol, or alpha-tocopherol and gamma-tocopherol, or beta-tocopherol and gamma-tocopherol, or alpha-tocopherol and ascorbic acid, or beta-tocopherol and ascorbic acid, or gamma-tocopherol and ascorbic acid.

According to a further preferred embodiment, the present invention comprises a mixture of beta-tocopherol, alpha-tocopherol and gamma-tocopherol.

Further Additives

It is to be understood that other physiologically safe additives may also be present in the composition according to the invention including, but not limited to, salts commonly used for intravenous application such as sodium chloride and nonelectrolytes such as glucose, pH modifiers (such as acetic acid and sodium acetate) and buffers (such as acetate, lactate, and phosphate buffer systems composed of the acid and a salt of the acid) as well as selenium compounds.

One skilled in the art will understand that the pH of the composition may for example be adjusted through the use of buffers, such as phosphate buffers, or neutralization agents, such as sodium hydroxide.

Preferably, the composition according to the present invention has a pH value close to physiological pH or above since it is contemplated that at such pH values the fatty acids are less prone to peroxidation.

The final pH of the composition is preferably in the range of from 7.0 to 10, preferably in the range of from 8 to 10.

By way of example, the composition may further comprise other additives conventionally used in pharmaceutical compositions. Such additives include carbohydrate nutrients, electrolytes, amino acids, vitamins, trace minerals, preservatives, anti-foaming agents, buffering agents, chelating agents, and mixtures thereof. The amounts of such additives can be readily determined by one skilled in the art according to the particular properties desired.

The Method for Preparing the Composition

As described above, the present invention also relates to a method for preparing a composition for parenteral administration and to a composition obtained or obtainable by said method the composition comprising an aqueous phase and 5 to 30% by weight of an oil phase, based on the total weight of the composition, wherein the oil phase comprises omega-3 fatty acids selected from the group consisting of eicosapentaenoic acid triglyceride, docosahexaenoic acid triglyceride and mixtures thereof, and wherein the composition further comprises at least one amphoteric surfactant, at least one co-surfactant and at least one co-solvent, wherein the method comprises:
(a) providing an aqueous phase comprising the at least one co-solvent and the at least one amphoteric surfactant,
(b) providing an oil phase comprising omega-3 fatty acid triglycerides selected from the group consisting of eicosapentaenoic acid triglyceride, docosahexaenoic acid triglyceride and mixtures thereof,
(c) mixing the oil phase according to (b) with the aqueous phase according to (a),
wherein the at least one co-surfactant is added either in step (b) or in step (c), and wherein less than 0.03% by weight of sodium oleate based on the total weight of the final composition are added during the method.

It is to be understood that any one of the optional further components of the composition may be added in any one of steps (a) to (c), or in one or more additional steps.

Step (a)

Step (a) is preferably carried out by mixing the at least one co-solvent and the at least one amphoteric surfactant together or subsequently with water. This step is preferably carried out at a temperature in the range of from 25 to 70° C., wherein during this step, the temperature may be varied or held essentially constant.

Preferably, initially, the at least one co-solvent is mixed with water.

Preferably, subsequently, the at least one amphoteric surfactant is added to the mixture comprising water and the at least one co-solvent thereby forming a dispersion. Preferably, the resulting mixture is mixed for example with a high shear mixer.

Preferably, the mixture is then heated to a temperature in the range of from 40 to 70° C., preferably, 50 to 65° C., more preferably 55 to 60° C., preferably for a time in the range of from 1 min to 2 h, more preferably of from 5 min to 1 h, more preferably of from 10 min to 15 min.

It is to be understood that in step (a) further additives may be added.

For example, in case the composition comprises at least one tonicity agent, this may be in principle added in any step of the method described above. According to one preferred embodiment, this additive, if present, is added in step (a). Thus, preferably step (a) further comprises mixing at least one tonicity agent with water, more preferably mixing glycerol with water. These additives may mixed with water prior to or after the addition of the at least one co-solvent and/or the at least one amphoteric surfactant. More preferably, these additives are mixed with water prior to or after the addition of the at least one co-solvent.

Preferably, step (a) further comprises adjusting the pH of the aqueous phase, such as through the use of buffers, such as phosphate buffers, or neutralization agents, such as sodium hydroxide, to a desired pH which is preferably in the range of from 7.0 to 10, more preferably in the range of from 8 to 10.

Step (b)

As outlined above, initially a mixture comprising EPA and DHA triglycerides is provided, wherein the EPA and DHA triglycerides may be obtained by any way known to those skilled in the art.

Preferably, the oil phase is heated in step (b), that is prior to step (c), to a temperature in the range of from 30 to 70° C., more preferably from 40 to 65° C., more preferably from 50 to 60° C., more preferably to a temperature around 55° C., preferably for a time in the range of from 1 min to 30 min, more preferably from 3 min to 20 min, more preferably from 5 min to 15 min.

Preferably, in step (b), the at least one co-surfactant is added. In case the oil phase is heated, the co-surfactant may be added prior to, during or after the heating step. Preferably, the co-surfactant is added during the heating step.

The oil phase is preferably homogenized, preferably at a temperature in range of from 30 to 70° C., more preferably from 40 to 65° C., more preferably from 50 to 60° C., more preferably to a temperature around 55° C.

According to a preferred embodiment, at least one agent with antioxidant activity, if present, is additionally added in step (b). Thus, in this case, in step (b) optionally at least one co-surfactant and optionally at least one agent with antioxidant activity are added to the mixture of EPA triglycerides and DHA triglycerides, more preferably oleic acid and/or at least one tocopherol are added in step (b).

Thus, step (b) preferably comprises providing an oil phase by mixing eicosapentaenoic acid triglycerides and docosahexaenoic acid triglycerides with the at least one co-surfactant and/or the at least one agent with antioxidant activity, wherein at least 60% by weight of the oil phase consist of eicosapentaenoic acid triglycerides and docosahexaenoic acid triglycerides. Alternatively, the provided mixture comprising EPA and DHA triglycerides may already comprise the or at least part of the total amount of the at least one co-surfactant and/or the at least one agent with antioxidant activity.

Step (c)

The method further comprises mixing the oil phase according to (b) with the aqueous phase according to (a) to give a mixture of oil phase and an aqueous phase. Preferably, thereby a pre-emulsion or an emulsion is formed. The mixing may be carried out by any methods known to those skilled in the art. Preferably, the mixing is carried out using a high shear mixer.

Preferably, the oil phase is added to the aqueous phase or vice versa at a temperature in the range of from 50 to 70° C., more preferably from 55 to 65° C.

Preferably the oil phase is added to the aqueous phase or vice versa at a pressure, such as under nitrogen pressure, in the range of from 0.20 to 0.80 bar, more preferably from 0.20 to 0.40 bar, such as at around 0.30 bar. During this step, pressure may be varied or held essentially constant.

According to a preferred embodiment, the mixture is stirred for a time in the range of from 1 min to 1 h, preferably of from 10 min to 30 min, to give a pre-emulsion. During this step, the temperature may be varied or held essentially constant.

It is to be understood that further components may also be added after the formation of the pre-emulsion. According to a preferred embodiment, the pH of the pre-emulsion is adjusted to a pH in the range of from 8 to 10, in particular by adding sodium hydroxide, if necessary.

Step (d)

Preferably, the method further comprises the homogenization of the mixture obtained from step (c). This homogenization may be carried out by any suitable methods known to those skilled in the art.

Preferably, the mixture is homogenized at temperature in range of from 40 to 70° C., more preferably from 50 to 70° C., more preferably from 50 to 60° C.

Preferably, the mixture is homogenized at a pressure in the range of from 400 to 600 bar, more preferably from 450 to 550 bar, During this step, the pressure may be varied or held essentially constant. During this step, the pressure may be varied or held essentially constant.

Preferably, the homogenization may for example be carried out using a high pressure homogenizer or a microfluidizer.

Thus, the present invention also relates to a method as described above for preparing a composition for parenteral administration, as well as to a composition obtained or obtainable by said method, the method further comprising:

(d) homogenizing the mixture, preferably the pre-emulsion, obtained from (c) at a temperature in the range of from 50 to 60° C. and at a pressure at a pressure in the range of from 400 to 600 bar.

After the homogenization step, further steps may be carried out, such as purification steps or filtration steps.

Step (e)

Preferably, the composition obtained in (c) or (d) is sterilized to ensure its suitability for parenteral administration.

The sterilization may be carried out by any suitable methods known to those skilled in the art. In particular, the sterilization is carried out by autoclaving, preferably at a temperature in the range of from 119° C. to 122° C., more preferably at a temperature of around 121° C., preferably for a time in the range of from 1 min to 30 min preferably of from 10 min to 15 min.

Thus, the present invention also relates to a method as described above for preparing a composition for parenteral administration as well as to a composition obtained or obtainable by said method, the method further comprising (e) autoclaving the mixture obtained from (c) or (d), preferably from (d), at a temperature in the range of from 119° C. to 122° C. for a time in the range of from 10 min to 15 min.

It is to be understood that the preparation of the composition preferably takes place under GMP standardized conditions in order to ensure quality, safety and effectiveness of the composition when used as a medicament or in parenteral nutrition. Further criteria for an ingredient or a composition being pharmaceutically acceptable can be derived from approval regulations by a regulatory agency and/or generally recognized pharmacopoeias.

As described above, the present invention also relates to a composition for parenteral administration as described above, or a composition for parenteral administration obtained or obtainable by the above described method, for use as a medicament. Further, the present invention relates to a medicament comprising the composition for parenteral administration as described above, or a composition for parenteral administration obtained or obtainable by the above described method. Further, the present invention relates to a composition for parenteral administration as described above, or a composition for parenteral administration obtained or obtainable by the above described method, for use in providing nutrition to a patient in need thereof.

The term "parenteral administration" as used herein means that the administration is not through the gastrointestinal tract, but rather through some other route, such as via the subcutaneous, intramuscular, intravenous, intradermal or intraspinal route. "Intravenous" is understood to mean administration into a venous blood vessel.

Preferably, the composition as described above, or the composition obtained or obtainable by the above described method, is administered intravenously. "Intravenous" is understood to mean administration into a venous blood vessel.

The composition may be injected or administered via infusion. Injection refers to administration using a syringe. Generally, a bolus is administered. However, injection or infusion by means of syringe-pumps is also possible. The term "infusion" refers to the continuous administration of the composition into a blood vessel which, for example, can be effected via a peripheral or central venous catheter.

Preferably, the composition as described above, or the composition obtained or obtainable by the above described method, is administered via infusion. Thus, according to a preferred embodiment, the present invention also relates to an infusion bag comprising the composition as described above, or the composition obtained or obtainable by the above described method.

It is to be understood that the preparation of the composition preferably takes place under GMP standardized conditions in order to ensure quality, pharmaceutical regulations safety and effectiveness of the composition when used as a medicament or in parenteral nutrition. Further criteria for an ingredient or a composition being pharmaceutically acceptable can be derived from approval regulations by a regulatory agency and/or generally recognized pharmacopoeias.

As described above, the present invention also relates to a composition as described above, or a composition for parenteral administration obtained or obtainable by the above described method, for use as a medicament. Preferably, the said composition is administered parenterally.

Further the present invention relates to a medicament comprising the composition for parenteral administration as described above, or a composition for parenteral administration obtained or obtainable by the above described method. Further, the present invention relates to a composition for parenteral administration as described above, or a composition for parenteral administration obtained or obtainable by the above described method, for use in providing nutrition to a patient in need thereof.

The term "parenterally" as used herein refers to a mode of administration. Preferably, the term includes subcutaneous, intramuscular, intravenous, intradermal or intraspinal administration. Preferably, the term does not encompass administration through the gastrointestinal tract, in particular through oral administration.

It is to be understood that the composition of the present invention is administered in an effective amount, in particular in a therapeutically effective amount, i.e. in an amount which allows for the treatment of a disease as referred to herein below. Whether an amount of the composition is effective or not can be determined by the skilled person without further ado.

Preferably, the present invention also relates to a composition for parenteral administration as described above, or a composition for parenteral administration obtained or obtainable by the above described method, for use in treating stroke, sepsis, Alzheimer's disease or cancer. Further, the present invention also relates to a composition for parenteral administration as described above, or a composition for parenteral administration obtained or obtainable by the above described method, for use in providing nutrition to a patient suffering from at least one disease selected from stroke, sepsis, Alzheimer's disease or cancer.

Likewise, the present invention also relates to a method for treating stroke, sepsis, Alzheimer's disease or cancer comprising parenterally administering the composition as described above, or the composition obtained or obtainable by the above described method, to a patient in need thereof. Further, the present invention relates to a method of providing parenteral nutrition to a patient suffering from at least one disease selected from stroke, sepsis, Alzheimer's disease or cancer, the method comprising administering a composition as described above, or a composition obtained or obtainable by the above described method, preferably parenterally, more preferably intravenously, to the patient.

The term "treatment" or "treating" as used herein in the context of treating a disease pertains generally to treatment and therapy of a patient in which some desired therapeutic effect is achieved, for example the inhibition of the progress of a symptom associated with a disease, such as stroke, sepsis, Alzheimer's disease or cancer, and includes a reduction in the rate of progress, a halt in the rate of progress, amelioration of the symptom, and cure of the symptom. Treatment as a prophylactic measure (i.e. prophylaxis) is also included.

Preferably, the composition according to the present invention is used for the treatment and/or for the parenteral nutrition of a human patient. Preferably, the patient shall suffer from at least one disease selected from the group consisting of stroke, sepsis, Alzheimer's disease and cancer.

According to a preferred embodiment, the present invention relates to a composition for parenteral administration as described above, or a composition for parenteral administration obtained or obtainable by the above described method, for use in treating stroke.

Stroke is the rapidly developing loss of brain function(s) due to disturbance in the blood supply to the brain. This can be due to ischemia (lack of blood flow) caused by blockage (thrombosis, arterial embolism), or a hemorrhage (leakage of blood). The etiology of stroke is either ischemic, as in the majority of cases, or hemorrhagic. Ischemic stroke is usually caused by an embolus or a thrombus. The methods of the invention encompass treatment of either ischemic or hemorrhagic stroke via intravenous administration of the compositions described herein. After a massive cell death in the immediate core of the infarct caused by glucose and oxygen deficiency (cerebral ischemia), the zone of infarction grows for a few days due to secondary mechanisms such as glutamate excitotoxicity, inflammatory mechanisms, the production of free radicals and apoptotic mechanisms. The methods of the invention encompass prevention and/or reduction of these secondary mechanisms to reduce the zone of infarction by intravenous administration of the compositions described herein. According to a further embodiment, the present invention relates to a composition for parenteral administration as described above, or a composition for parenteral administration obtained or obtainable by the above described method, for use in in providing nutrition to a patient suffering from stroke. Further, the present invention relates to a method of providing parenteral nutrition to a patient suffering from stroke.

According to a further embodiment, the present invention relates to a composition for parenteral administration as described above, or a composition for parenteral administration obtained or obtainable by the above described method, for use in treating cancer. For example, it has been suggested that omega-3 fatty acids can improve the response to chemotherapy of various cancers by enhancing cytotoxicity of anti-cancer drugs and by reducing oxidative stress. Thus, it is contemplated that the compositions of the present invention can improve the clinical outcomes by accentuating the response to primary cytotoxic drugs in cancer therapy. Further, the present invention relates to a composition for parenteral administration as described above, or a composition for parenteral administration obtained or obtainable by the above described method, for use in providing nutrition to a patient suffering from cancer. Further, the present invention relates to a method of providing parenteral nutrition to a patient suffering cancer.

According to a further embodiment, the present invention relates to a composition for parenteral administration as described above, or a composition for parenteral administration obtained or obtainable by the above described method, for use in treating sepsis, in particular for treatment for endotoxicosis during severe sepsis, or for use in providing nutrition to a patient suffering from sepsis. Further, the present invention relates to a method of providing parenteral nutrition to a patient suffering from sepsis.

The term "sepsis" as used herein refers to a medical condition which is caused by the response of the immune system to an infection. This response is called systemic inflammatory response syndrome (SIRS). Sepsis can proceed to severe sepsis, septic shock, refractory septic shock or multi-organ dysfunction syndrome (MODS). The latter conditions are associated with organ dysfunction, e.g. the cardiovascular, the renal, the respiratory, the cerebral or the hematologic system.

According to a further embodiment, the present invention relates to a composition for parenteral administration as described above, or a composition for parenteral administration obtained or obtainable by the above described method, for use in treating Alzheimer's disease or for use in providing nutrition to a patient suffering from Alzheimer's disease. Further, the present invention relates to a method of providing parenteral nutrition to a patient suffering from Alzheimer's disease.

The term "Alzheimer's disease" is well known in the art. As used herein, the term refers to a progressive mental deterioration which is manifested by memory loss, confusion and disorientation. The disease is usually beginning in late middle life and results in death within five to ten years. Alzheimer's disease can be diagnosed by methods well known in the art. It is characterized by thickening, conglutination, and distortion of the intracellular neurofibrils, neurofibrillary tangles and senile plaques composed of granular or filamentous argentophilic masses with an amyloid core.

In the following, especially preferred embodiments of the present invention are described by way of example:

1. A composition for parenteral administration comprising an aqueous phase and 5 to 30% by weight of an oil phase, based on the total weight of the composition, wherein the oil phase comprises omega-3 fatty acid triglycerides selected from the group consisting of eicosapentaenoic acid triglycerides, docosahexaenoic acid triglycerides and mixtures thereof, and wherein the composition further comprises at least one amphoteric surfactant, at least one co-surfactant and at least one co-solvent, and wherein the composition comprises less than 0.03% by weight of sodium oleate, based on the total weight of the composition.
2. The composition according to embodiment 1, wherein at least 60% by weight of the oil phase consist of omega-3 fatty acid triglycerides selected from the group consisting of eicosapentaenoic acid triglycerides, docosahexaenoic acid triglycerides and mixtures thereof.
3. The composition according to embodiment 1 or 2, wherein the oil phase comprises a mixture of eicosapentaenoic acid triglycerides and docosahexaenoic acid triglycerides and wherein the weight ratio of eicosapentaenoic acid triglycerides to docosahexaenoic acid tryiglycerides is in the range of from 1 to 9 to 9 to 1.
4. The composition according any one of embodiments 1 to 3, wherein the oil phase comprises less than 1% by weight medium chain triglycerides based on the total weight of the composition.
5. The composition according to any one of embodiments 1 to 4, being an oil-in-water emulsion having a mean droplet particle size in the range of from 0.1-0.3 µm measured with a LS 13 320 Laser Diffraction Particle Size Analyser (Beckman Coulter) according to USP <729>.
6. The composition according to any one of embodiments 1 to 5, comprising at least one agent with antioxidant activity, preferably at least two agents with antioxidant activity.
7. The composition according to embodiment 6, wherein the at least one agent with antioxidant activity is selected from the group consisting of alpha-tocopherol, beta-tocopherol, gamma-tocopherol, ascorbic acid, ascorbic acid palmitate, an antioxidant obtained or obtainable from rosemary, rosemary extract and mixtures of two or more thereof.
8. The composition according to embodiment 6 or 7, wherein the total amount of agents with antioxidant activity is in the range of from 0.01 to 0.05% by weight, based on the total weight of the composition.
9. The composition according to any one of embodiments 1 to 8, wherein the at least one amphoteric surfactant is lecithin.
10. The composition according embodiment 9, wherein the lecithin is selected from the group consisting of egg lecithin, soy lecithin, and mixtures thereof.
11. The composition according to embodiment 9 or 10, wherein the total amount of lecithin is in the range of from 1 to 2% by weight, based on the total weight of the composition.
12. The composition according any one of embodiments 1 to 11, wherein the at least one co-surfactant, is an omega-9 fatty acid, preferably a monounsaturated omega-9 fatty acid, more preferably oleic acid.
13. The composition according to any one of embodiments 1 to 12, wherein the total amount of the at least one co-surfactant is in the range of from 0.03 to 0.5% by weight, based on the total weight of the composition.
14. The composition according to any one of embodiments 1 to 13 wherein the composition comprises at least one tonicity agent.

15. The composition according embodiment 14, wherein the tonicity agent is glycerol.
16. The composition according to embodiment 14 or 15, wherein the total amount of the at least one tonicity agent is in the range of from 1 to 3% by weight based on the total weight of the composition.
17. The composition according to any one of embodiments 14 to 16, wherein the composition has an osmolality in the range 305-420 mOsmol/kg measured with a Vapor Pressure Osmometer, Model 5520 (Vapro™) according to USP <785>.
18. The composition according to any one of embodiments 1 to 17, wherein the at least one co-solvent is polyethylene glycol.
19. The composition according embodiment 18, wherein the polyethylene glycol has a mean molecular weight in the range of from 300 to 600 Da.
20. The composition according to embodiment 18 or 19, wherein the total amount of polyethylene glycol is in the range of from 0.5 to 2.0% by weight, based on the total weight of the composition.
21. The composition according to any one of embodiments 1 to 3, wherein the composition comprises less than 0.02% by weight, more preferably less than 0.01% by weight, more preferably essentially no sodium oleate.
22. A method for preparing a composition for parenteral administration comprising an aqueous phase and 5 to 30% by weight of an oil phase, based on the total weight of the composition, wherein the oil phase comprises omega-3 fatty acids selected from the group consisting of eicosapentaenoic acid triglyceride, docosahexaenoic acid triglyceride and mixtures thereof, and wherein the composition further comprises at least one co-surfactant, at least one co-solvent and at least one amphoteric surfactant, wherein the method comprises:
    (a) providing an aqueous phase, comprising the at least one co-solvent and the at least one amphoteric surfactant,
    (b) providing an oil phase comprising omega-3 fatty acid triglycerides selected from the group consisting of eicosapentaenoic acid triglyceride, docosahexaenoic acid triglyceride and mixtures thereof,
    (c) mixing the oil phase according to (b) with the aqueous phase according to (a), wherein the at least one co-surfactant is added either in step (b) or in step (c), and wherein less than 0.03% by weight of sodium oleate, based on the total weight of the final composition, are added during the method.
23. The method according to embodiment 22, wherein the oil phase is heated to 55° C. for a time in the range of 5 min to 15 min prior to step (c).
24. The method according to embodiment 22 or 23, wherein step (b) further comprises the addition of the at least one co-surfactant to the oil phase.
25. The method according to any one of embodiments 22 to 24, further comprising:
    (d) homogenizing the mixture obtained from (c) at a temperature in the range of from 50 to 60° C. at a pressure in the range of from 450 to 550 bar.
26. The method according to any one of embodiments 22 to 25, further comprising:
    (e) autoclaving the mixture obtained from (c) or (d), preferably from (d), at a temperature in the range of from 119° C. to 122° C. for a time in the range of from 10 min to 15 min.
27. A composition obtained or obtainable by the method according to any one of embodiments 22 to 26.
28. A composition according to any one of embodiments 1 to 21 or 27 for use as a medicament.
29. A composition according to any one of embodiments 1 to 21 or 27 for use in treating stroke, sepsis, Alzheimer's disease or cancer.
30. The composition according to embodiment 28 or 29, wherein the composition is administered parenterally.
31. The composition according to embodiment 30, wherein the composition is administered intravenously.
32. A method for treating stroke, sepsis, Alzheimer's disease or cancer comprising intravenously administering the composition according to any one of embodiments 1 to 21 or 27 to a patient in need thereof.
33. An infusion bag comprising the composition according to any one of embodiments 1 to 21 or 27.
34. A medicament comprising the composition according to any one of embodiments 1 to 21 or 27.
35. A method for treating stroke, sepsis, Alzheimer's disease or cancer comprising intravenously administering the composition according to any one of embodiments 1 to 21 or 27 in a pharmaceutically effective amount to a patient in need thereof.
36. A method of providing parenteral nutrition to a patient suffering from at least one disease selected from stroke, sepsis, Alzheimer's disease or cancer, the method comprising administering the composition according to any one of embodiments 1 to 21 or 27 to the patient.
37. The method of embodiments 35 or 36, wherein the composition is administered parenterally.
38. A composition according to any one of claim 1 to 21 or 27 for use in providing parenteral nutrition to a patient suffering from at least one disease selected from stroke, sepsis, Alzheimer's disease or cancer.

FIGURES

FIG. 1 shows the droplet size distribution after 1 week and after 3 weeks of composition 1 (as depicted in table 2, containing mixture 1) prepared according to general procedure A containing 10% by weight of the oil phase (see Table 1) measured with a LS 13 320 Laser Diffraction Particle Size Analyser (Beckman Coulter) according to USP <729>. The results comply with the requirements set forth in USP <729>.

The following examples are intended to illustrate the present invention without limiting it.

EXAMPLES

Different mixtures comprising highly concentrated omega-3 fatty acids (eicosapentaenoic acid (EPA) and docosahexaenoic acid (DHA)) as triglycerides as obtained from Solutex S.L were used.
Mixture 1:
EPA triglyceride (g/g) 0.697
DHA triglyceride (g/g) 0.124
Mixture 2:
EPA triglyceride (g/g) 0.2027
DHA triglyceride (g/g) 0.4674
Mixture 3:
EPA triglyceride (g/g) 0.0747
DHA triglyceride (g/g) 0.6406

Example 1

General Procedure A for the Preparation of an Emulsion According to the Invention Using a shear mixer, lecithin (PL90, obtainable from egg yolk=egg lecithin with a phosphatidylcholine content of 64-79% and a phosphatidylethanolamine content of 10-18% by weight) was dispersed in water for injection, at a temperature between 55-60° C., previously containing glycerol and polyethylene glycol (PEG), using a Rayneri TURBO-TEST high shear mixer, until a homogeneous dispersion was obtained. Afterwards, the pH of the aqueous dispersion was adjusted to 9-10. The oil phase, containing different ratios of docosahexaenoic acid/eicosapentanoic acid triglycerides (mixtures 1 to 3), was heated to 55° C. and, then, oleic acid was added until a clear and homogeneous solution was obtained. The aqueous dispersion was then transferred to a separate container and the oil phase was added under continuous stirring, using a Rayneri TURBOTEST high shear mixer, to obtain coarse oil-in-water emulsions with oil phase concentrations comprised between 10-30 wt. The coarse emulsions were then passed six times through a homogenizer (Niro Soavi Panda Plus 2000) at 500 bar and a temperature between 50-60° C. Finally, the emulsions were autoclaved at 122° C. for 15 min. Final lipid emulsions were obtained. The mean particle size of the lipid emulsions was measured using a Malvern Mastersizer 2000.

TABLE 1

Composition of a formulation prepared according to example 1

| Ingredients | Weight-% |
|---|---|
| Triglyceride - EPA/DHA | 10 |
| Egg lecithin | 1.2 |
| Oleic acid | 0.15 |
| Glycerol | 2.25 |
| Polyethylene glycol PEG 400 | 1.0 |
| Water for injection | adds up to 100 |
| Properties: | |
| pH release | 8-8.7 |
| Surface mean droplet diameter D [3, 2] | ≤0.3 |
| Volume weighted mean diameter D [4, 3] | ≤0.3 |
| % Droplets > 5 micrometer | ≤0.05 |

Further compositions prepared are given in Table 2. For some of these compositions, no stable emulsions could be obtained. Surprisingly, in particular emulsions comprising a combination of PEG, oleic acid and lecithin turned out to be particularly stable.

TABLE 2

Examples of compositions tested and some relevant parameters

| | 1 a, b, c | 2 a, b, c | 3 a, b, c | 4 a, b, c | 5 a, b, c | 6 a, b, c | 7 a, b, c | 8 a, b, c | 9 a, b, c |
|---|---|---|---|---|---|---|---|---|---|
| DHA/EPA [weight.-%] | 10 Mixtures 1, 2, 3 | 10 Mixtures 1, 2, 3 | 10 Mixtures 1, 2, 3 | 10 Mixtures 1, 2, 3 | 10 Mixtures 1, 2, 3 | 10 Mixtures 1, 2, 3 | 10 Mixtures 1, 2, 3 | 10 Mixtures 1, 2, 3 | 10 Mixtures 1, 2, 3 |
| Egg lecithin [weight.-%] | 1.2 | 1.2 | 1.2 | 1.2 | 1.2 | 1.2 | 1.2 | 1.2 | 1.2 |
| Glycerol [weight.-%] | 2.25 | 2.25 | 2.5 | 2.5 | 2.5 | 2.25 | 2.5 | 2.5 | 2.5 |
| Tocopherols [weight.-%] | 0.02 | 0.02 | 0.02 | 0.02 | 0.02 | 0.02 | 0.02 | 0.02 | 0.02 |
| Oleic Acid [weight.-%] | 0.15 | 0.15 | — | — | — | 0.15 | 0.12 | 0.12 | 0.12 |
| Sodium Oleate [weight.-%] | — | — | 0.2 | 0.3 | 0.03 | — | 0.18 | 0.03 | 0.2 |
| PEG 400 [weight.-%] | 1 | 2 | — | — | — | — | — | — | — |
| Propylene glycol [weight.-%] | — | — | — | — | — | 1 | — | — | — |
| Water for injection [weight.-%] | Adds up to 100 | Adds up to 100 | Adds up to 100 | Adds up to 100 | Adds up to 100 | Adds up to 100 | Adds up to 100 | Adds up to 100 | Adds up to 100 |
| Stable Emulsion Y = yes; N = no | Y | Y | N After some weeks | N After some weeks | N After some weeks | Y | N spontaneous | N spontaneous | N spontaneous |
| pH release | 8.7 | 8.8 | 8.6 | 9.4 | 8.5 | 8.6 | 8.8 | 8.3 | 8.9 |
| Surface mean droplet diameter D [3, 2] | ≤0.3 | ≤0.3 | ≤0.3 | ≤0.3 | ≤0.3 | ≤0.3 | >0.03 | >0.03 | >0.03 |
| Volume weighted mean diameter D [4, 3] | ≤0.3 | ≤0.3 | ≤0.3 | ≤0.3 | ≤0.3 | ≤0.3 | >0.03 | >0.03 | >0.03 |
| % Droplets > 5 micrometer | ≤0.05 | ≤0.05 | >0.05 | >0.05 | >0.05 | ≤0.05 | >0.05 | >0.05 | >0.05 |

The invention claimed is:

1. A composition comprising
an aqueous phase and 5 to 30% by weight of an oil phase, based on the total weight of the composition, wherein the oil phase comprises eicosapentaenoic acid triglycerides, docosahexaenoic acid triglycerides or mixtures thereof and less than 1% by weight medium chain triglycerides, based on the total weight of the composition and wherein the composition further comprises
an amphoteric surfactant comprising lecithin;
a co-surfactant comprising oleic acid; and
a co-solvent comprising polyethylene glycol, wherein the composition is formulated for parenteral administration and comprises less than 0.03% by weight of sodium oleate, based on the total weight of the composition.

2. The composition of claim 1, wherein at least 60% by weight of the oil phase consists of eicosapentaenoic acid triglycerides, docosahexaenoic acid triglycerides or mixtures thereof.

3. The composition of claim 1, wherein the oil phase comprises a mixture of eicosapentaenoic acid triglycerides and docosahexaenoic acid triglycerides and the weight ratio of the eicosapentaenoic acid triglycerides to the docosahexaenoic acid triglycerides is in the range of from 1 to 9 to 9 to 1.

4. The composition of claim 1, further comprising an agent with antioxidant activity.

5. The composition of claim 4, wherein the agent with antioxidant activity is alpha-tocopherol, beta-tocopherol, gamma-tocopherol, ascorbic acid, ascorbic acid palmitate, an antioxidant obtained or obtainable from rosemary or rosemary extract, or mixtures thereof, wherein the total amount of the agent or agents with antioxidant activity is in the range of from 0.01 to 0.05% by weight, based on the total weight of the composition.

6. The composition of claim 1, wherein the composition further comprises a tonicity agent.

7. The composition of claim 1, wherein the composition comprises less than 0.02% by weight of the sodium oleate.

8. An infusion bag comprising the composition of claim 1.

9. The composition of claim 6, wherein the tonicity agent is glycerol.

* * * * *